US008920747B2

(12) United States Patent
Matsuura et al.

(10) Patent No.: US 8,920,747 B2
(45) Date of Patent: Dec. 30, 2014

(54) BIOSENSOR AND BIOSENSOR MANUFACTURING METHOD

(75) Inventors: Yoshimitsu Matsuura, Kyoto (JP); Shuzo Kanda, Koka (JP)

(73) Assignee: ARKRAY, Inc., Kyoto (JP)

(*) Notice: Subject to any disclaimer, the term of this patent is extended or adjusted under 35 U.S.C. 154(b) by 186 days.

(21) Appl. No.: 13/180,016

(22) Filed: Jul. 11, 2011

(65) Prior Publication Data

US 2012/0009611 A1    Jan. 12, 2012

Related U.S. Application Data

(60) Provisional application No. 61/363,467, filed on Jul. 12, 2010.

(30) Foreign Application Priority Data

Jul. 12, 2010  (JP) ................................. 2010-158243
Jul. 8, 2011   (JP) ................................. 2011-151428

(51) Int. Cl.
*G01N 33/48*    (2006.01)
*G01N 27/447*   (2006.01)
*G01N 27/327*   (2006.01)
*G01N 21/03*    (2006.01)
*G01N 35/00*    (2006.01)

(52) U.S. Cl.
CPC ...... *G01N 27/3272* (2013.01); *G01N 27/44743* (2013.01); *B01L 2400/0406* (2013.01); *B01L 2300/161* (2013.01); *B01L 2300/08* (2013.01); *B01L 2300/0825* (2013.01); *G01N 2021/0346* (2013.01); *G01N 2035/00108* (2013.01)
USPC .......... 422/412; 422/506; 422/520; 422/546; 422/564; 436/170

(58) Field of Classification Search
CPC .................... B01L 2400/0406; B01L 2300/08; B01L 2300/0825; B01L 2300/161; G01N 2021/0346; G01N 2035/00108; G01N 27/44743
USPC ........... 422/412, 506, 520, 546, 564; 436/170
See application file for complete search history.

(56) References Cited

U.S. PATENT DOCUMENTS 6,033,627 A * 3/2000 Shields et al. ................ 422/408
7,312,042 B1  12/2007 Petyt et al.
(Continued)

FOREIGN PATENT DOCUMENTS

EP   0 924 520 A2   6/1999
EP   1 203 956 A2   5/2002
(Continued)

OTHER PUBLICATIONS

The Extended European Search Report dated Nov. 7, 2011; EP Application No. 11173688.0-2204.
(Continued)

*Primary Examiner* — Lyle Alexander
(74) *Attorney, Agent, or Firm* — Studebaker & Brackett PC

(57) ABSTRACT

A biosensor manufacturing method including a sheet material forming process and a dicing process. In the sheet material forming process a sheet material with plural biosensor forming sections is formed. Each of the biosensor forming sections includes a first base plate, a second base plate stacked on the first base plate and forming a capillary between the second base plate and the leading end portion of the first base plate for sucking in sample liquid, and a hydrophilic layer formed on the second base plate at least in a region facing the capillary. In the dicing process plural biosensors are obtained by dicing the sheet material with a blade from the first base plate side at the leading end of each of the biosensor forming sections, such that the leading end of the capillary opens onto the leading end face of the first base plate and the second base plate.

7 Claims, 7 Drawing Sheets

(56) References Cited

U.S. PATENT DOCUMENTS

| | | | |
|---|---|---|---|
| 8,007,645 B2 | 8/2011 | Yamanishi et al. | |
| 2003/0196894 A1 | 10/2003 | Cai et al. | |
| 2005/0098433 A1* | 5/2005 | Gundel | 204/403.02 |
| 2006/0057740 A1 | 3/2006 | Hiroshi et al. | |
| 2008/0101983 A1 | 5/2008 | Petyt et al. | |
| 2010/0078322 A1 | 4/2010 | Yamanishi et al. | |
| 2013/0031772 A1 | 2/2013 | Petyt et al. | |

FOREIGN PATENT DOCUMENTS

| | | |
|---|---|---|
| EP | 1 211 321 A1 | 6/2002 |
| JP | 2004-184180 A | 7/2004 |
| JP | 2007-003361 A | 1/2007 |
| JP | 2007-3361 A | 1/2007 |
| JP | 2008-175795 A | 7/2008 |
| JP | 2009-229469 A | 10/2009 |
| JP | 2010-507805 A | 3/2010 |

OTHER PUBLICATIONS

An Office Action; "Notice of Reasons for Rejection," issued by the Japanese Patent Office on Aug. 6, 2013, which corresponds to Japanese Patent Application No. 2011-151428 and is related to U.S. Appl No. 13/180,016; with translation.

* cited by examiner

BIOSENSOR AND BIOSENSOR MANUFACTURING METHOD

CROSS-REFERENCE TO RELATED APPLICATION

This application is based on and claims priority under 35 USC 119 from Japanese Patent Application No. 2010-158243 filed on Jul. 12, 2010, Japanese Patent Application No. 2011-151428 filed on Jul. 8, 2011, and U.S. Provisional Application No. 61/363,467 filed on Jul. 12, 2010, which are incorporated by reference herein.

BACKGROUND

1. Technical Field

The present invention relates to a biosensor and to a biosensor manufacturing method.

2. Related Art

A biosensor is described in Japanese Patent Application Laid-Open (JP-A) No. 2007-3361 that is configured with a first insulating base plate and a second insulating base plate stuck onto the first insulating base plate and forming a capillary between the second insulating base plate and a leading end portion of the first insulating base plate for sucking in a sample liquid.

In the field of such types of biosensor a known biosensor manufacturing method obtains plural biosensor by dicing a sheet material. Traditionally in such a biosensor manufacturing method a blade is inserted from the second insulating base plate side so as to obtain plural biosensors.

However, in such cases a burr is formed on the second insulating base plate projecting out towards the capillary side, leading to concern of a drop in capillary sucking ability.

SUMMARY

The present invention is made in consideration of the above issue, and is directed towards a biosensor and biosensor manufacturing method capable of securing the sucking ability of the capillary.

A biosensor manufacturing method according to an aspect of the invention includes: a sheet material forming process that forms a sheet material with a plurality of biosensor forming sections, each of the biosensor forming sections including a first base plate, a second base plate stacked on the first base plate and forming a capillary between the second base plate and a leading end portion of the first base plate for sucking in sample liquid, and a hydrophilic layer formed on the second base plate at least in a region facing the capillary; and a dicing process to obtain a plurality of biosensors by dicing the sheet material with a blade from the first base plate side at the leading end of each of the biosensor forming sections, such that a leading end of the capillary opens onto the leading end face of the first base plate and the second base plate.

According to the above biosensor manufacturing method, due to the blade being inserted from the first base plate side, the opposite side to the second base plate formed with the hydrophilic layer, the burr on the second base plate induced during dicing can be suppressed from projecting out to the hydrophilic layer side. Delamination or damage to the hydrophilic layer can accordingly be suppressed from occurring during dicing, and the sucking ability of the capillary can be secured.

In the above biosensor manufacturing method, a first base plate with a higher toughness than the second base plate may be employed for the first base plate in the sheet material forming process.

According to the above biosensor manufacturing method, a first base plate of higher toughness than the second base plate is employed as the first base plate, and hence burring can be suppressed from occurring from the first base plate on the capillary side when the blade is inserted from the first base plate side. Obstacles to the sample liquid being sucked up by the capillary can be eliminated or reduced, and hence sucking ability of the capillary can be better secured.

However, the leading end portion of the first base plate is deformed towards the second base plate side when the blade is inserted from the first base plate side. Then, when the blade has been removed, the leading end portion of the first base plate returns towards its original shape. The face on the capillary side of the leading end portion of the first base plate accordingly slopes away from the second base plate on progression towards the leading end. The leading end side of the capillary is accordingly imparted with a cross-section dimension in the direction of stacking the first base plate and the second base plate that widens on progression towards the leading end. Consequently, even when the amount of sample liquid is small, for example, the sample liquid can be readily spotted on the leading end of the capillary, and the sample liquid can be sucked into the capillary without problems.

In the above biosensor manufacturing method, the leading end of each of the biosensor forming sections may be diced so that the leading end face of the first base plate is a face sloping toward a rear end side of the first base plate on progression away from the second base plate.

According to the above biosensor manufacturing method, the leading end face of the first base plate is configured with a face sloping towards the rear end side of the first base plate on progression away from the second base plate. The sample liquid is hence readily placed in contact with the hydrophilic layer when the sample liquid is being sucked up by the capillary, enabling the sample liquid to be sucked up into the capillary without problems.

In the above biosensor manufacturing method, a single faced blade may be employed as the blade in the dicing process, the single faced blade including a contact face for contact with the leading end faces of the first base plate and the second base plate configured as a face sloping towards the rear end side of the first base plate on progression from the second base plate towards the first base plate side.

According to the above biosensor manufacturing method, a single faced blade is employed with a contact face that makes contact with the leading end faces of the first base plate and the second base plate, and is a face sloping towards the rear end side of the first base plate on progression from the second base plate side towards the first base plate side. The leading end face of the first base plate can accordingly be placed after dicing further to the rear end side of the second base plate than the leading end face of the second base plate, with insertion of the blade also from the first base plate side. Consequently, interference can be suppressed between the holding body holding the sample liquid and the leading end face of the first base plate when the sample liquid is being sucked into the capillary, enabling the sample liquid to be sucked up into the capillary without problems.

In the above biosensor manufacturing method, a double faced blade may be employed as the blade in the dicing process, the double faced blade comprising a pair of blade portions next to each other along an array direction of a pair of biosensor forming sections to be diced.

According to the above biosensor manufacturing method, a double faced blade is employed as the blade, and the blade is also inserted from the first base plate side. The leading end face of the first base plate can accordingly be placed after dicing further to the rear end side of the second base plate than the leading end face of the second base plate. Consequently, interference can be suppressed between the holding body holding the sample liquid and the leading end face of the first base plate when the sample liquid is being sucked into the capillary, enabling the sample liquid to be sucked up into the capillary without problems.

According to another aspect, a biosensor includes: a first base plate; a second base plate stacked on the first base plate and forming a capillary between the second base plate and a leading end portion of the first base plate that is for sucking in a sample liquid; a hydrophilic layer formed on the second base plate at least in a region facing the capillary; and a burr extending out from the second base plate on the side away from the capillary.

According to the above biosensor, the burr is formed on the second base plate as the first base plate and the second base plate are being diced by the blade. The burr extends out from the opposite side of the second base plate to that of the capillary due to inserting the blade from the first base plate side. The burr on the second base plate can accordingly be suppressed from projecting out to the capillary side of the second base plate, this being the hydrophilic layer side. The sucking ability of the capillary can hence be secured.

In the above biosensor, the first base plate may be formed with higher toughness than the second base plate.

According to the above biosensor the first base plate has higher toughness than the second base plate. Accordingly, generation of a burr from the first base plate towards the capillary side can be suppressed when the blade is inserted from the first base plate side. Consequently, obstacles to the sample liquid being sucked up by the capillary can be eliminated or reduced. Consequently, sucking ability of the capillary can be better secured.

In the above biosensor, the leading end side of the capillary may have a cross-section dimension, in the direction of stacking the first base plate and the second base plate, which gets wider on progression toward the leading end.

According to the above biosensor, the cross-section dimension at the leading end side of the capillary in the direction of stacking the first base plate and the second base plate widens on progression towards the leading end. Consequently, for example, even if there is only a small amount of the sample liquid, the sample liquid can be readily spotted on the leading end of the capillary, and the sample liquid can be sucked into the capillary without problems.

In the above biosensor, the leading end face of the first base plate may be formed as a face sloping toward a rear end side of the first base plate on progression way from the second base plate.

According to the above biosensor, the leading end face of the first base plate is configured with a face sloping towards the rear end side of the first base plate on progression away from the second base plate. The sample liquid is accordingly readily placed in contact with the hydrophilic layer when the sample liquid is being sucked in by the capillary, enabling the sample liquid to be sucked up into the capillary without problems.

In the above biosensor, the leading end face of the first base plate may be disposed further to a rear end side of the second base plate than a leading end face of the second base plate.

According to the above biosensor, the leading end face of the first base plate is placed after dicing further to the rear end side of the second base plate than the leading end face of the second base plate. Consequently, interference can accordingly be suppressed between the holding body holding the sample liquid and the leading end face of the first base plate when the sample liquid is being sucked into the capillary, enabling the sample liquid to be sucked up into the capillary without problems.

In the above biosensor, a region on the first base plate facing the capillary may have either a test reagent or an electrode present.

According to the above biosensor, fast mixing of the sample liquid with the test reagent can be achieved.

In the above biosensor a region of the first base plate facing the capillary may be also provided with a hydrophilic layer.

According to the above biosensor, the sample liquid arrives faster at the reaction region, enabling reaction and measurement to be accomplished in a short period of time.

In the above biosensor blood may be sucked in as the sample liquid. Moreover, the above biosensor may be employed for measuring a blood sugar value.

The above biosensor sample liquid sucking method may include: spotting a sample liquid onto a leading end side of the capillary, such that the sample liquid is caused to creep along a face of the second base plate on a side facing the first base plate, and also caused to creep along a face of the first base plate on a side facing the second base plate.

As explained in detail above, according to the present invention the suction ability of the capillary can be secured.

BRIEF DESCRIPTION OF THE DRAWINGS

An exemplary embodiment of the present invention will be described in detail based on the following figures, wherein.

DETAILED DESCRIPTION

Explanation follows regarding an exemplary embodiment of the present invention, with reference to the drawings.

Figure 1:
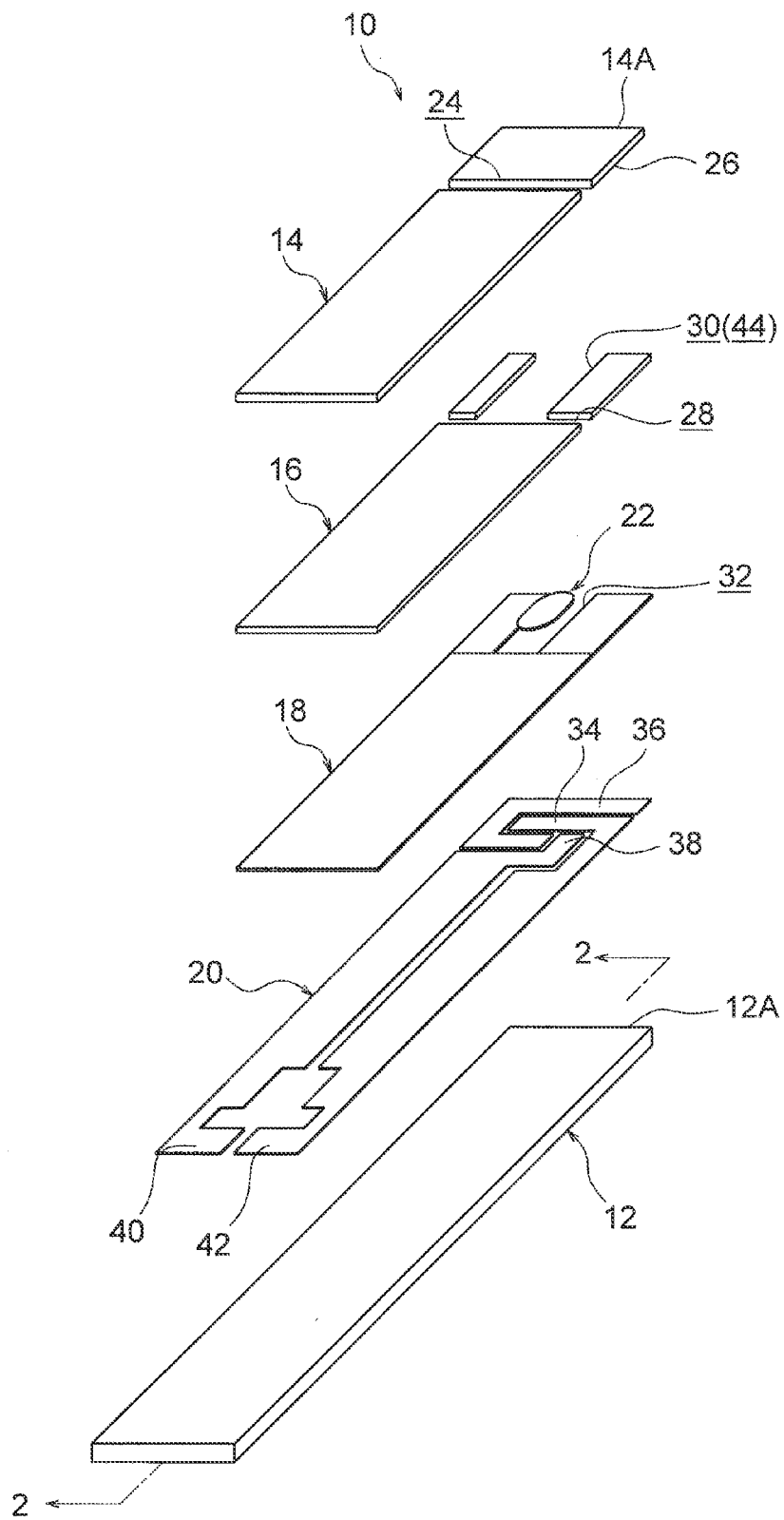
FIG. 1 is an exploded perspective view of a biosensor according to an exemplary embodiment of the present invention.
Figure 2:
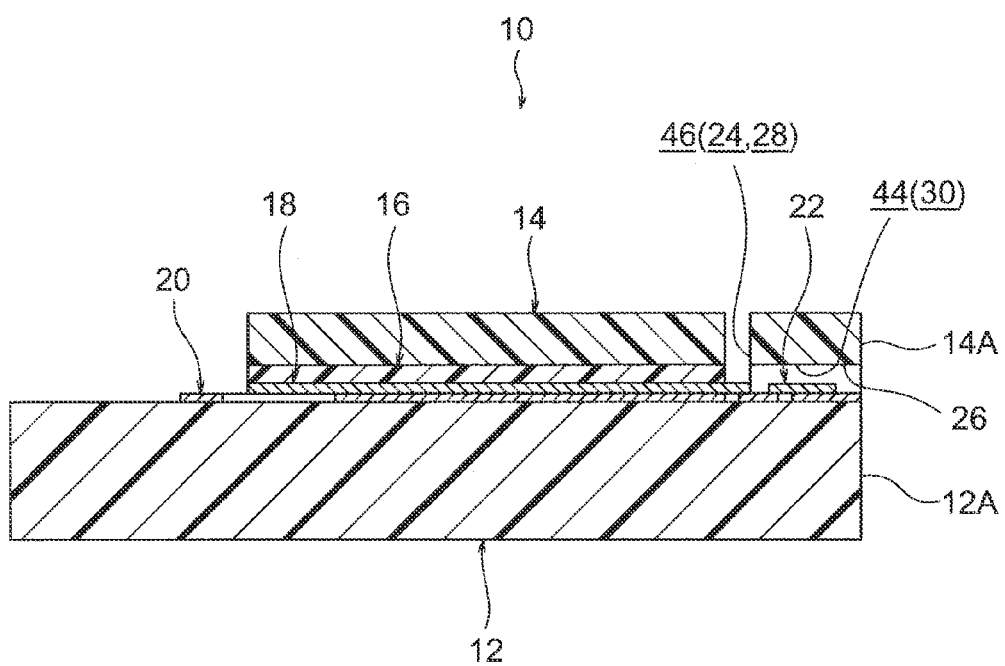
FIG. 2 is a cross-section taken on line 2-2 of the biosensor illustrated in FIG. 1.

A biosensor 10 according to an exemplary embodiment of the present invention, illustrated in FIG. 1 and FIG. 2, is, for example, a biosensor employed for taking and analyzing a sample liquid, such as blood. The biosensor 10 includes a first base plate 12, a second base plate 14, a spacer 16, a resist 18, a carbon electrode 20 and a test reagent 22.

The first base plate 12 and the second base plate 14 are each formed in an elongated rectangular shape, with the first base plate 12 formed with higher toughness than the second base plate 14. In the present exemplary embodiment, as an example, the first base plate 12 is formed from a stretchable resin film, such as polybutylene terephthalate (PBT). The second base plate 14 is, for example, formed by a resin tape, such as polyethylene terephthalate (PET). The Izod impact strengths (un-notched) of PBT and PET are 1794 (J/m) and 686 (J/m), respectively. Thus when the first base plate 12 is formed from PBT and the second base plate 14 is formed from PET the first base plate 12 has a higher toughness than the second base plate 14. A resin material is often employed for the material of the first base plate 12 (for example PBT, polyethylene terephthalate (PET), polycarbonate (PC), or polyvinyl alcohol (PVA)), however there is no limitation thereto. A resin material is often employed for the material of the second base plate 14 (for example PBT, PET, PC, or PVA) however there is no limitation thereto.

A slit 24 is formed at the leading end side of the second base plate 14, extending along the width direction of the second base plate 14. A hydrophilic layer 26 with hydrophilic properties is formed on the back face of the second base plate 14. The hydrophilic layer 26 may be formed over the entire back face of the second base plate 14, or may be formed locally in a region facing a capillary 44, described later below. Namely it is sufficient for the hydrophilic layer 26 to be formed on at least on a region facing the capillary 44. In the present exemplary embodiment the hydrophilic layer 26 is formed on the back face of the second base plate 14. However, configuration may be made with a hydrophilic layer formed on a region of the first base plate 12 facing the second base plate 14.

The spacer 16 is, for example, formed with double-sided adhesive tape extending along the second base plate 14. A slit 28 is formed at the leading end side of the spacer 16. The slit 28 is formed extending along the width direction of the spacer 16 at a location aligned with the slit 24. A cutout 30 is also formed in the spacer 16 further towards the leading end side than the slit 28 and extending along the length direction of the spacer 16. The cutout 30 is employed for configuring the capillary 44, described later, and is open to the leading end of the spacer 16.

The resist 18 is formed as a protective layer covering the front face of the carbon electrode 20. A cutout 32 is formed at the leading end side of the resist 18 in a location aligned with the above cutout 30. The carbon electrode 20 is configured with plural electrodes 34, 36, 38 and with leads 40, 42.

As shown from top to bottom in FIG. 2, all of the members described above are stacked on each other in the sequence of: the second base plate 14, the spacer 16, the resist 18, the carbon electrode 20, and the first base plate 12. When all of the members are stacked together in this state the capillary 44 is formed between leading end portions of the first base plate 12 and the second base plate 14 by the cutout 30. The capillary 44 is open to the leading end faces 12A, 14A of the first base plate 12 and the second base plate 14, respectively, and the capillary 44 also opens to the outside through an air gap 46 formed by the slits 24, 28.

A portion of each of the electrodes 34, 36, 38 shown in FIG. 1 is exposed through the cutout 32 in the capillary 44, and the test reagent 22 is placed in the capillary 44 so as to make contact with a portion of each of the electrodes 34, 36, 38. Namely configuration is made such that in the region on the first base plate 12 facing the capillary 44 either the test reagent 22 or one of the electrodes 34, 36, 38 is present.

The biosensor 10 sucks in sample liquid from the leading end of the capillary 44 by utilizing capillary action and hydrophilic attraction. When the sample liquid is introduced into the capillary 44 a change occurs in electrical properties due to a reaction between the sample liquid and the test reagent 22. In an analysis method using the biosensor 10 the leads 40, 42 are connected to a measurement instrument, and analysis of the sample liquid is performed by the measurement instrument detecting such changes in electrical properties.

Explanation follows regarding a manufacturing method for the biosensor 10 configured as described above, together with explanation of the characteristic configuration of the biosensor 10 achieved using this manufacturing method.

Figure 4:
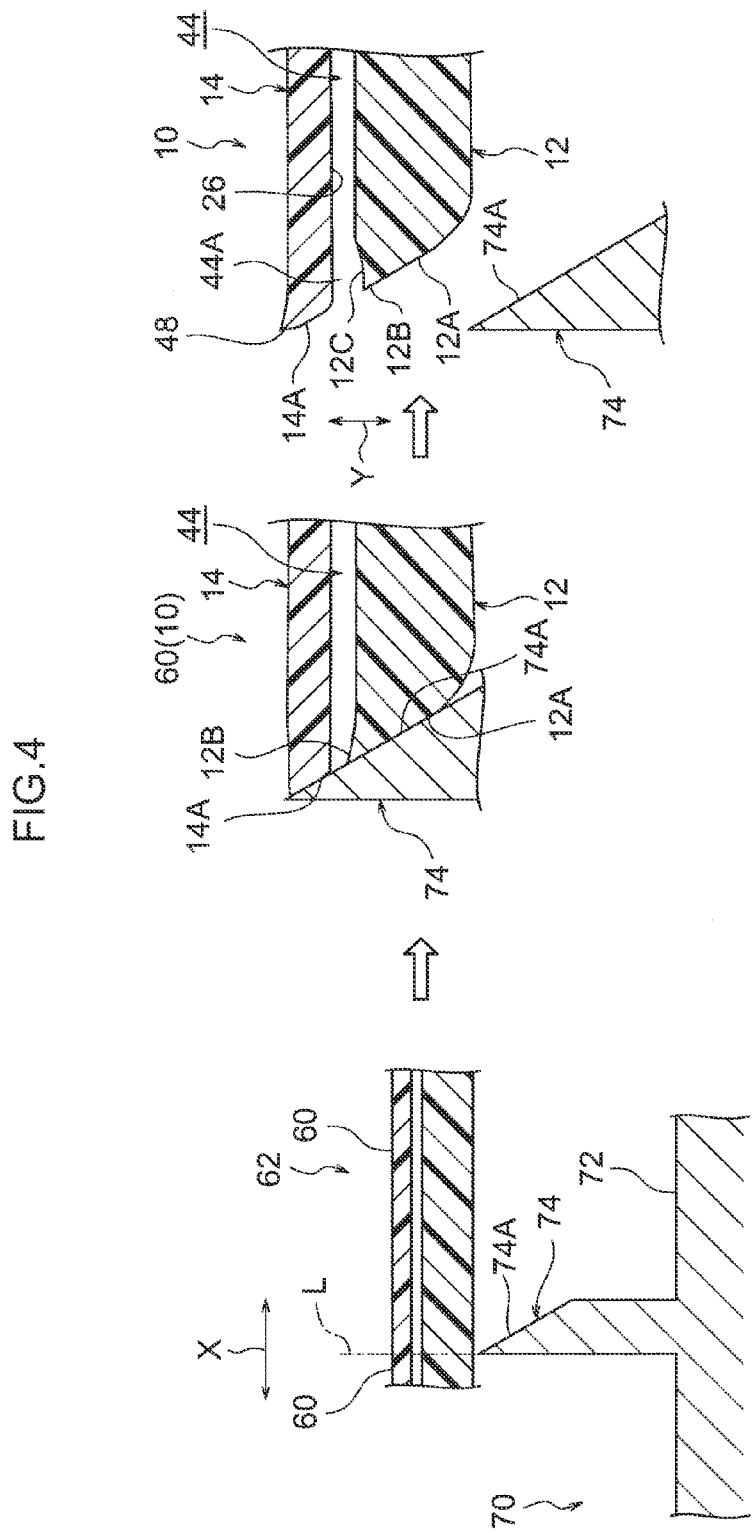
FIG. 4 is an explanatory diagram of the flow of a manufacturing method for the biosensor illustrated in FIG. 1.

Namely, in the manufacturing method of the biosensor according to the exemplary embodiment of the present invention, as shown on the left hand side of FIG. 4, first a sheet material 62 is formed with plural biosensor forming sections 60 that will become the base of the biosensor 10 (see FIG. 1). The dotted line L illustrated on the left hand side of FIG. 4 indicates a boundary between biosensor forming sections 60.

Each of the biosensor forming sections 60 is configured with the first base plate 12, the second base plate 14, the spacer 16, the resist 18, the carbon electrode 20 and the test reagent 22, as illustrated in FIG. 1. The first base plate 12 has imparted with higher toughness than the second base plate 14 by utilizing materials such as those of the examples given above. The above processes correspond to the sheet material forming process of the present invention.

Figure 5:
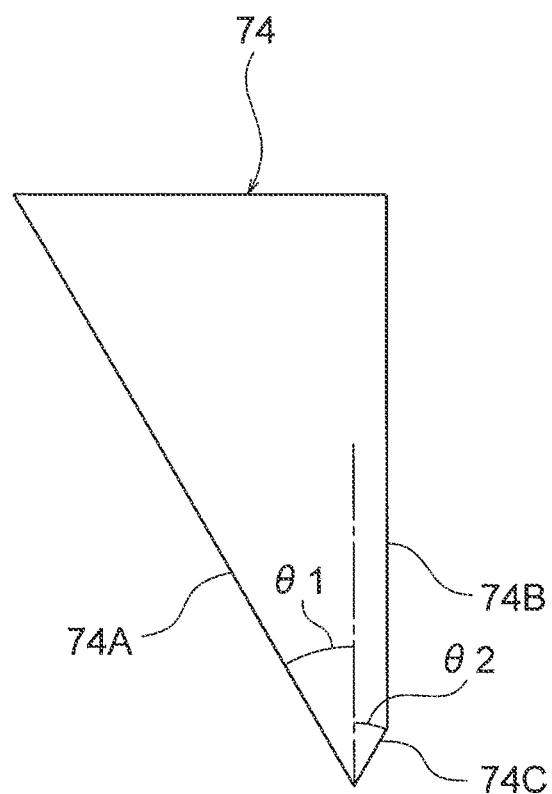
FIG. 5 is an enlarged diagram of the blade illustrated in FIG. 4.

The sheet material 62 is then diced. The following processes correspond to the dicing process of the present invention. A fabrication device 70 is employed in dicing the sheet material 62, such as the one shown on the left hand side of FIG. 4. The fabrication device 70 is configured with a mold 72 and a single blade 74 formed to the mold 72. The blade 74 employs a single face blade, with a contact face 74A that makes contact with the leading end faces 12A, 14A of the first base plate 12 and the second base plate 14. The blade 74 is a face sloping towards the rear end side of the first base plate 12 on progression from the second base plate 14 side towards the first base plate 12 side. The blade 74 is, as shown in FIG. 5, formed with a face 74B on the opposite side of the blade 74 to the contact face 74A. The face 74B is parallel to the blade insertion direction. A reinforcement face 74C is formed at the blade tip side of the contact face 74A. In the present exemplary embodiment the blade tip angles $\theta 1, \theta 2$ of the blade 74 are, for example, formed at 30°. These angles $\theta$ may be anything from 5° to 50°, are preferably from 10° to 40°, and are more preferably from 15° to 30°.

As shown at the center and on the right hand side of FIG. 4, the sheet material 62 is diced by the blade 74 at the leading end of each of the biosensor forming sections 60 from the first base plate 12 side, such that the leading end of the capillary 44 is opened to the leading end faces 12A, 14A of the first base plate 12 and the second base plate 14.

As shown at the center of FIG. 4, the leading end portion 12B of the first base plate 12 is deformed towards the second base plate 14 side when the blade 74 is inserted from the first base plate 12 side. Then, when the blade 74 has been removed, as shown on the right hand side of FIG. 4, the leading end portion 12B of the first base plate 12 returns towards its original shape. A face 12C is thereby formed on the capillary 44 side of the leading end portion 12B of the first base plate 12. The face 12C slopes away from the second base plate 14 on progression towards the leading end. The leading end side 44A of the capillary 44 is accordingly imparted with a cross-section dimension in the direction of stacking the first base plate 12 and the second base plate 14 (arrow Y direction) that widens in on progression towards the leading end.

Figure 3:
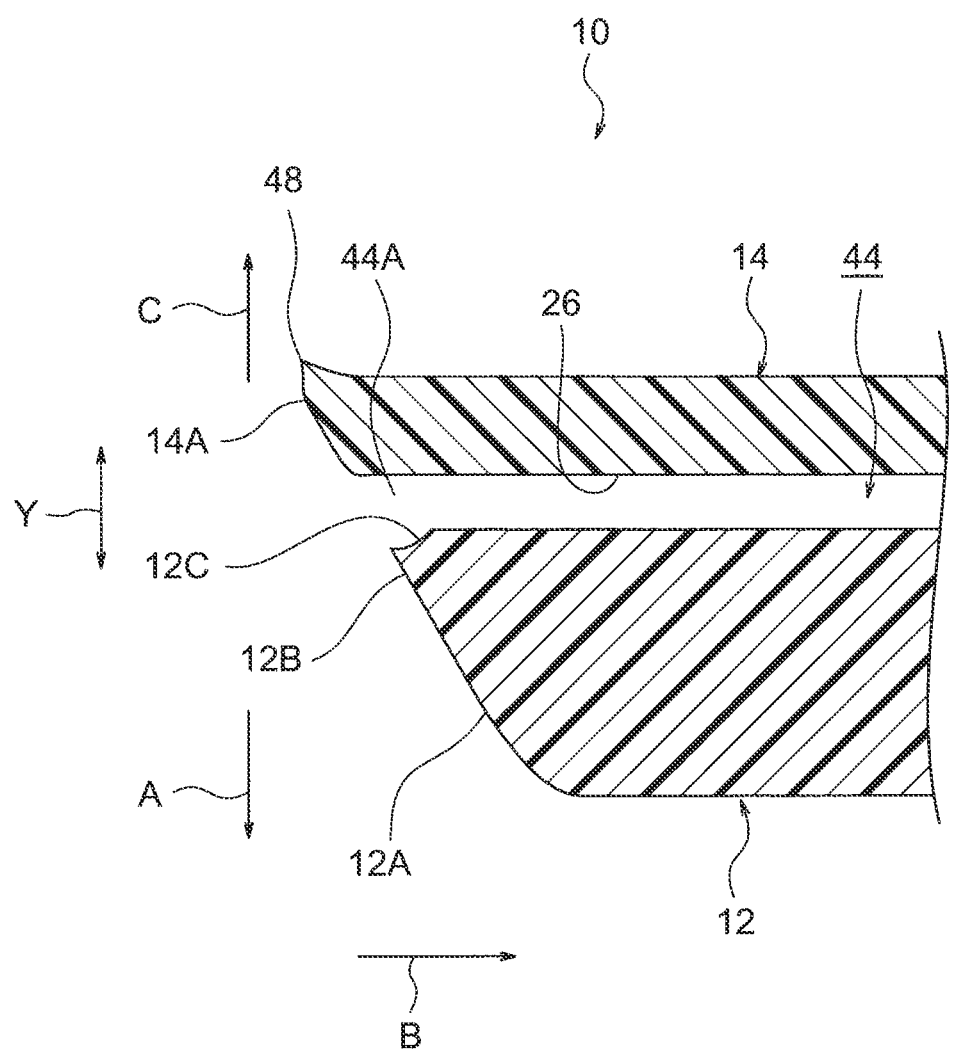
FIG. 3 is an enlarged cross-section of relevant portions at a leading end portion of the biosensor illustrated in FIG. 1.

As shown at the center of FIG. 4, the blade 74 is inserted to cut in parallel to the direction of stacking of the first base plate 12 and the second base plate 14. The contact face 74A of the blade 74 is a sloping face inclined to the blade insertion direction. The leading end face 12A of the first base plate 12 after dicing is accordingly formed as a sloping face that slopes towards the rear end side of the first base plate 12 (the arrow B direction in FIG. 3) on progression away from the second base plate 14 (the arrow A direction in FIG. 3).

Namely, the leading end of each of the biosensor forming sections 60 is diced such that the leading end face 12A of the first base plate 12 configures a face sloping towards the rear end side of the first base plate 12 on progression away from the second base plate 14.

Furthermore, as shown on the right hand side of FIG. 4, a burr 48 is formed to the second base plate 14 as the first base plate 12 and the second base plate 14 are being diced with the blade 74 from the first base plate 12 side. The burr 48 is formed so as to project out towards the front in the insertion direction of the blade 74 (the arrow C direction side in FIG. 3). Namely, the burr 48 project out from the second base plate 14 away from the capillary 44.

By utilizing a single faced blade as described above as the blade 74, after dicing the leading end face 12A of the first base plate 12 is positioned further to the rear end side of the second base plate 14 than the leading end face 14A of the second base plate 14 (the arrow B direction side in FIG. 3) when the blade 74 is inserted from the first base plate 12 side.

Plural of the biosensors 10 are obtained from the sheet material 62 by performing the above.

Explanation follows next regarding operation and effect of the exemplary embodiment of the present invention.

As described in detail above, according to the biosensor manufacturing method of the exemplary embodiment of the present invention, by inserting the blade 74 from the first base plate 12 side, this being opposite side of the second base plate 14 to that formed with the hydrophilic layer 26, the burr on the second base plate 14 induced during dicing can be suppressed from projecting out to the hydrophilic layer 26 side of the second base plate 14. Delamination or damage to the hydrophilic layer 26 can accordingly be suppressed from occurring during dicing.

Namely, according to the biosensor 10 fabricated by the above manufacturing method, the burr 48 is formed on the second base plate 14 as the first base plate 12 and the second base plate 14 are being diced by the blade 74. The burr 48 extends out from the opposite side of the second base plate 14 to that of the capillary 44 due to inserting the blade 74 from the first base plate 12 side. The burr 48 of the second base plate 14 can accordingly be suppressed from projecting out to the capillary 44 side of the second base plate 14, this being the hydrophilic layer 26 side. The sucking ability of the capillary 44 can hence be secured.

In this biosensor manufacturing method the first base plate 12 is employed with higher toughness than the second base plate 14. Accordingly, generation of a burr on the first base plate 12 towards the capillary 44 side can be suppressed when the blade 74 is inserted from the first base plate 12 side. Consequently, according to the biosensor 10 fabricated by the above manufacturing method, obstacles to the sample liquid being sucked up by the capillary 44 can be eliminated or reduced. Consequently, sucking ability of the capillary 44 can be better secured. Occurrences of poor sucking with the biosensor are reduced as follows. The rate of poor sucking occurring is reduced from 42/8000 strips prior to widening structure change to 0/36740 strips after change.

According to the biosensor 10, the cross-section dimension at the leading end side 44A of the capillary 44 in the direction of stacking the first base plate 12 and the second base plate 14 widens on progression towards the leading end. Consequently, for example, even if there is only a small amount of the sample liquid, the sample liquid can be readily spotted on the leading end of the capillary 44, and the sample liquid can be sucked into the capillary 44 without problems.

According to the biosensor manufacturing method, the leading end face 12A of the first base plate 12 is configured with a face sloping towards the rear end side of the first base plate 12 on progression away from the second base plate 14.

According to the biosensor 10 fabricated by the above manufacturing method, the sample liquid is readily placed in contact with the hydrophilic layer 26 when the sample liquid is being sucked up by the capillary 44, enabling the sample liquid to be sucked up into the capillary 44 without problems.

According to the biosensor manufacturing method, by employing a single faced blade like the one described above for the blade 74, the leading end face 12A of the first base plate 12 can be placed after dicing further to the rear end side of the second base plate 14 than the leading end face 14A, with insertion of the blade 74 also from the first base plate 12 side. Consequently, according to the biosensor 10 fabricated by the above manufacturing method, interference can be suppressed between the holding body holding the sample liquid and the leading end face 12A of the first base plate 12 when the sample liquid is being sucked into the capillary 44, enabling the sample liquid to be sucked up into the capillary 44 without problems. The holding body referred to here corresponds, for example, to a fingertip when the sample liquid is a drop of blood on a fingertip.

The region of the first base plate 12 facing the capillary 44 is configured with either the test reagent 22 or the electrodes 34, 36, 38 present, enabling the sample liquid to be speedily mixed with the test reagent 22.

Note that the faces on which the electrodes 34, 36, 38 are placed may also be provided with a hydrophilic layer. However, good transportation of the sample liquid is achieved when a hydrophilic layer is formed on the face opposing the electrodes 34, 36, 38, or on both faces, by making the hydrophilicity of the face opposing the electrodes higher. Seedy mixing and even mixing with the test reagent 22 is thereby achieved, enabling accurate readings to be made in a short period of time.

A double faced blade 75 may be employed in the dicing process described above, as shown in FIG. 6. The blade 75 has a pair of blade portions 76 next to each other along the array direction of a pair of biosensor forming sections 60 to be diced (the arrow X direction). As shown in FIG. 7, the blade tip angles $\theta 1$, $\theta 2$, are, for example, each formed at 30°, thereby providing the blade 75 with sloped faces 75A, 75B on both sides. These angles $\theta 1$, $\theta 2$ may be anything within the range from 5° to 50°, are preferably from 10° to 40°, and more preferably from 15° to 30°.

Figure 6:
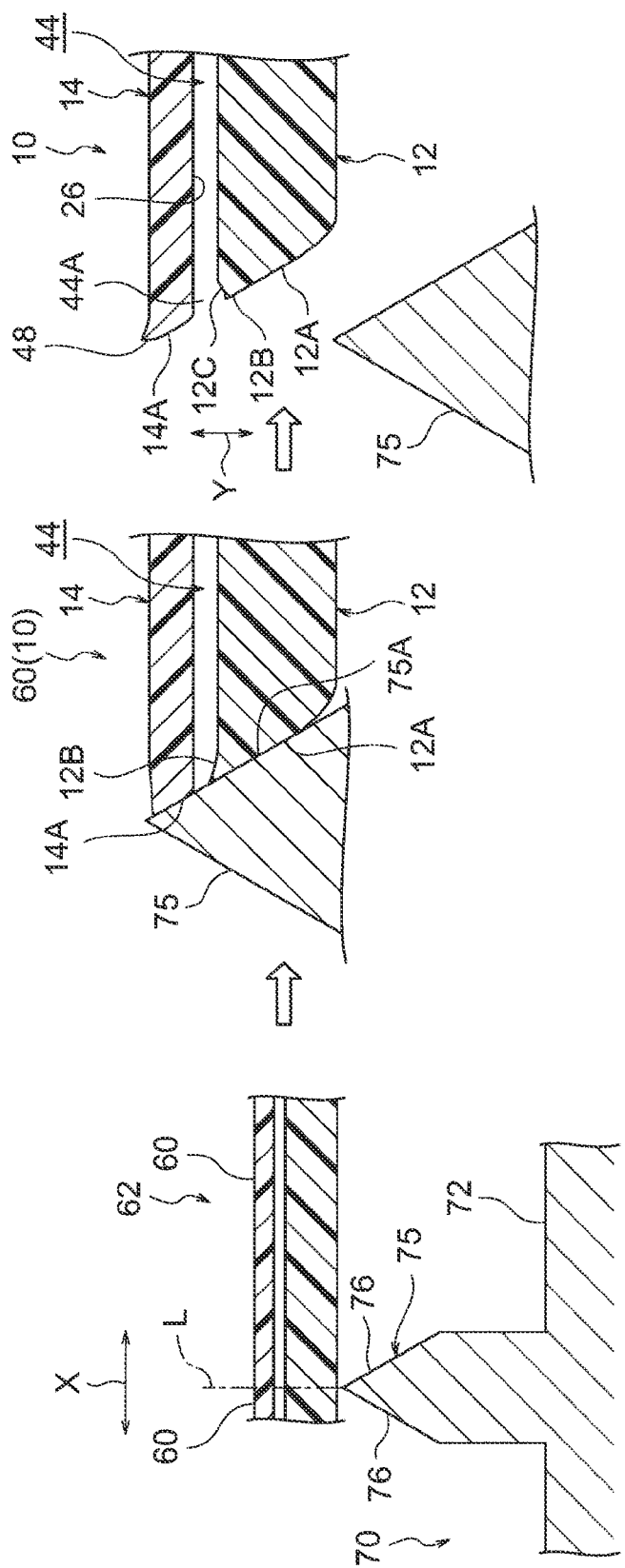
FIG. 6 is an explanatory diagram of the flow in a modified example of a manufacturing method of the biosensor illustrated in FIG. 1.
Figure 7:
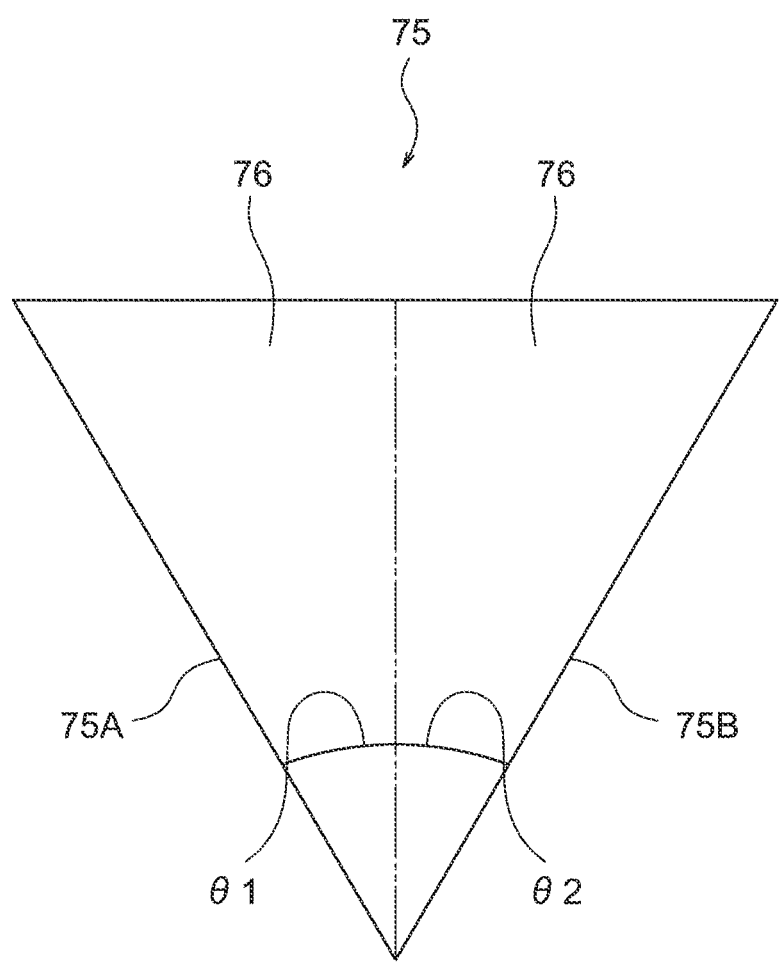
FIG. 7 is an enlarged diagram of the blade illustrated in FIG. 6.

The double faced blade in the present invention is a blade formed with left-right symmetry in FIG. 6, and the single faced blade in the present invention is formed as a blade that is asymmetrical in the left-right direction in FIG. 4, with one of its faces configured as a face sloping with respect to the blade insertion direction.

Also when the blade 75 is inserted from the first base plate 12 side, as shown in FIG. 6, the leading end face 12A of the first base plate 12 can be positioned further to the rear end side of the second base plate 14 than the leading end face 14A of the second base plate 14. Accordingly interference between the holding body for holding the sample liquid and the leading end face 12A of the first base plate 12 when the sample liquid is being sucked into the capillary 44 can be suppressed, enabling the sample liquid to be sucked into the capillary 44 without problems.

The blade 74 can employ a single faced blade with its sloping face on the side facing towards the capillary 44. However, when the blade 75 is employed the compression load from inserting the blade tip is more evenly dissipated than when a single faced blade is employed. The durability of the blade tip can accordingly be raised, and hence productivity when using the blade can also be raised. A reduction in cost can also be achieved by reducing blade changes caused by blade tip chipping, and by raising the durability of the blade.

The material used for the blade may, as an example be a metal, and treatment may be performed in order to raise the hardness and durability of the blade tip (for example quenching treatment, titanium treatment, diamond treatment), however there is no limitation thereto.

In comparison to processing by knocking out of a mold, the initial investment required is reduced since a complicated mold is not required, and the durability of the mold employed can be raised. Each of the manufacturing processes can also be simplified, and since there is no need to employ a high hardness blade this also enables a reduction in cost to be achieved.

By configuration with the hydrophilic layer formed on the first base plate 12 in the region facing the capillary 44 the sample liquid arrives at the reaction region faster, enabling reaction and measurement to be accomplished in a short period of time.

The sample liquid in the present invention includes, for example, a body fluid, and in particular blood and urine. Substances to be measured include, for example, substances such as glucose, lactic acid, cholesterol and uric acid. The structure of the above exemplary embodiment that increases suction force is particularly advantageous for viscous sample liquids in particular, such as blood. Due to the viscous nature of hematocrit and blood corpuscles affecting blood sugar measurements the structure of the above exemplary embodiment that increases suction force is useful for blood sugar value measurements.

The biosensor 10 of the present exemplary embodiment is preferably employed for sucking in blood as the sample liquid, and for measuring blood sugar values. Namely, while generally the viscosity of blood as the sample liquid can be accommodated, for blood sugar value measurements where there is a requirement for a particularly short response time the shape and characteristics of the biosensor configured as described above delivers an advantage.

Regarding the sample liquid sucking method of the biosensor 10, preferably the sample liquid is spotted on the leading end side 44A of the capillary 44, and the sample liquid is caused to creep along the face of the second base plate 14 on the first base plate 12 side and the sample liquid is also caused to creep along the face of the first base plate 12 on the second base plate 14 side.

The present invention is explained above by way of exemplary embodiments, however the present invention is not limited by the above, and obviously various modifications may be implemented within a range not departing from the spirit of the invention.

What is claimed is:

1. A biosensor manufacturing method comprising:
   a sheet material forming process that forms a sheet material with a plurality of biosensor forming sections, each of the biosensor forming sections comprising a first base plate, a second base plate stacked on the first base plate in a thickness direction and forming a capillary between the second base plate and a leading end portion of the first base plate for sucking in sample liquid, and a hydrophilic layer formed on the second base plate at least in a region facing the capillary; and
   a dicing process to obtain a plurality of biosensors by dicing the sheet material with a blade being inserted from the first base plate side at the leading end of each of the biosensor forming sections so that the leading end face of the first base plate at the capillary side is formed to slope away from the second base plate in the thickness direction after removal of the blade such that the capillary opens onto and widens in the thickness direction leading end portion has a wider opening than the subsequent capillary channel and the leading edge of the second base plate side protrudes beyond the leading edge of the first base plate toward the leading end face of the first base plate and the second base plate.

2. The biosensor manufacturing method of claim 1, wherein a first base plate with a higher toughness than the second base plate is employed for the first base plate in the sheet material forming process.

3. The biosensor manufacturing method of claim 1, wherein the leading end of each of the biosensor forming sections is diced so that the leading end face of the first base plate is a face sloping toward a rear end side of the first base plate on progression away from the second base plate.

4. The biosensor manufacturing method of claim 1, wherein a single faced blade is employed as the blade in the dicing process, the single faced blade comprising a contact face for contact with the leading end faces of the first base plate and the second base plate.

5. The biosensor manufacturing method of claim 1, wherein a double faced blade is employed as the blade in the dicing process, the double faced blade comprising a pair of blade portions next to each other along an array direction of a pair of biosensor forming sections to be diced.

6. The biosensor manufacturing method of claim 4, wherein the single faced blade has a first side and a second side and the first side is longer than the second side to create a sloped cutting surface of the contact face.

7. The biosensor manufacturing method of claim 1, wherein the leading end of each of the biosensor forming sections is diced so that the leading end face of the first base plate is disposed further to a rear end side of the second base plate than a leading end face of the second base plate.

* * * * *